United States Patent [19]

Thacker

[11] Patent Number: 5,024,222
[45] Date of Patent: Jun. 18, 1991

[54] HEMODYNAMICALLY RATE RESPONSIVE PACEMAKER AND METHOD OF AUTOMATICALLY ADJUSTING THE ESCAPE AND A-V INTERVALS

[75] Inventor: James R. Thacker, Canyon Country, Calif.

[73] Assignee: Siemens-Pacesetter, Inc., Sylmar, Calif.

[21] Appl. No.: 482,603

[22] Filed: Feb. 21, 1990

[51] Int. Cl.$^5$ ............................................. A61N 1/00
[52] U.S. Cl. ................................................ 128/419 PG
[58] Field of Search .............. 128/419 P, 419 PG, 734

[56] References Cited

U.S. PATENT DOCUMENTS

| | | | |
|---|---|---|---|
| 4,108,148 | 8/1978 | Cannon | 128/419 PG |
| 4,303,075 | 12/1981 | Heilman et al. | 128/419 PG |
| 4,467,807 | 8/1984 | Bornzin | 128/419 PG |
| 4,527,568 | 7/1985 | Rickards | 128/419 PG |
| 4,856,521 | 8/1989 | Irnich | 128/419 PG |
| 4,856,524 | 8/1989 | Baker, Jr. | 128/419 PG |
| 4,899,751 | 2/1990 | Cohen | 128/419 PG |
| 4,905,697 | 3/1990 | Heggs et al. | 128/419 PG |
| 4,907,593 | 3/1990 | Rapach et al. | 128/419 PG |
| 4,919,136 | 4/1990 | Alt | 128/419 P |

OTHER PUBLICATIONS

Furman, Seymour M.D., "AV Synchrony and Cardiac Rate," *PACE*, vol. 6 (May–Jun. 1983, Part 1), pp. 513–514.

Benditt, D. G. M.D. et al., "Sensor-Triggered, Rate-Variable Cardiac Pacing," *Annals of Internal Medicine* (1987), pp. 714–724.

Wirtzfeld, A. et al., "Central Venous Oxygen Saturation for the Control of Automatic Rate-Responsive Pacing," *PACE*, vol. 5 (Nov.–Dec. 1982), pp. 829–835.

*Primary Examiner*—Francis Jaworski
*Assistant Examiner*—George Manuel
*Attorney, Agent, or Firm*—Lisa P. Weinberg; Malcolm J. Romano

[57] ABSTRACT

In a rate responsive pacemaker, a physiological sensor is used to sense the physiological needs of the patient's heart and to control both the pacing rate and the A-V interval accordingly. A first adjustment means triggers the timing circuitry to adjust the stimulation rate to a slightly sub-optimal value of cardiac output. A second adjustment means adjusts the A-V interval until hemodynamics are optimized according to the physiological sensor. The improvement in hemodynamics due to the A-V adjustment allows a further decrease in the stimulation rate by the first adjustment means, thereby conserving the limited battery supply.

26 Claims, 5 Drawing Sheets

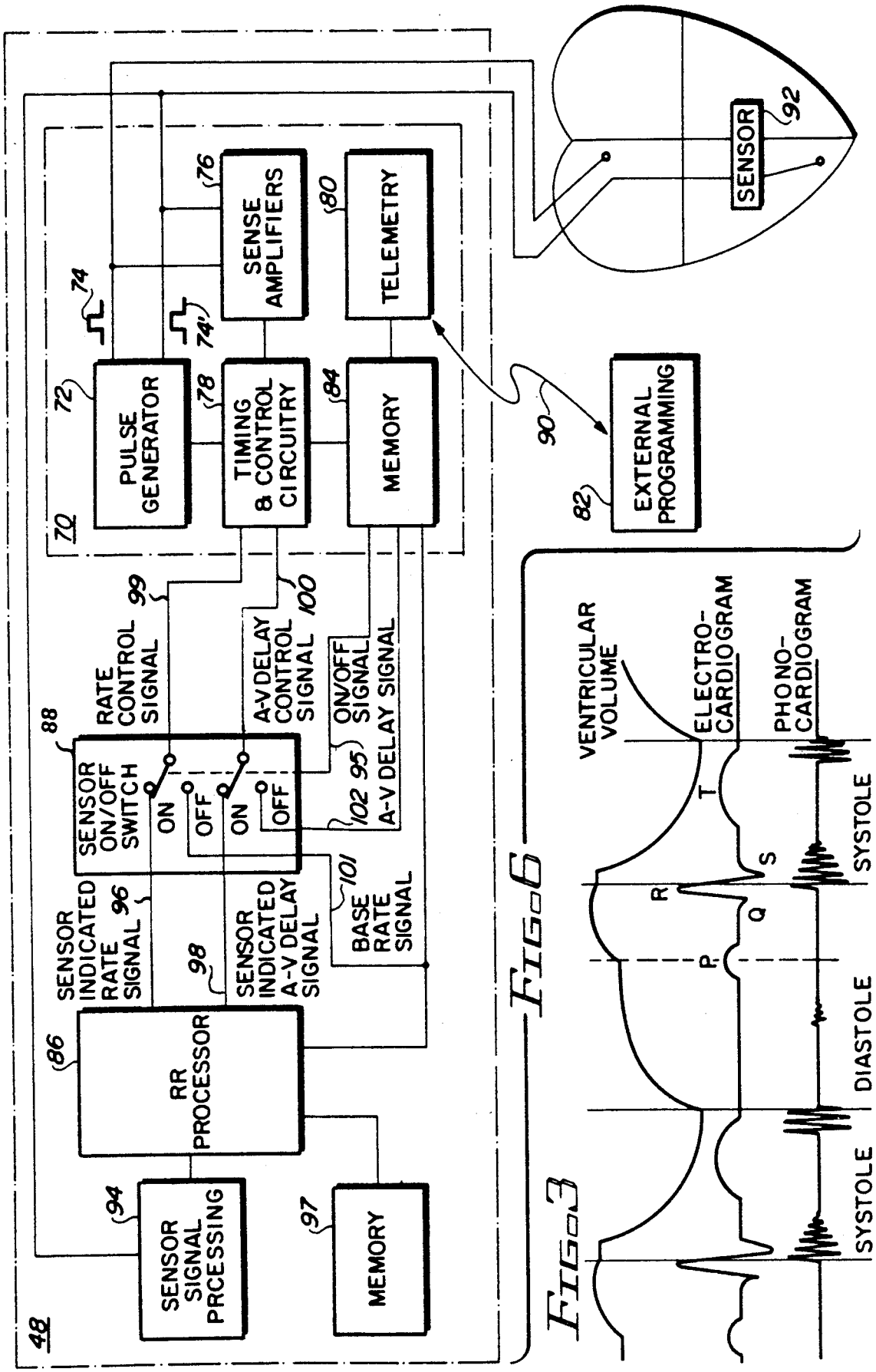

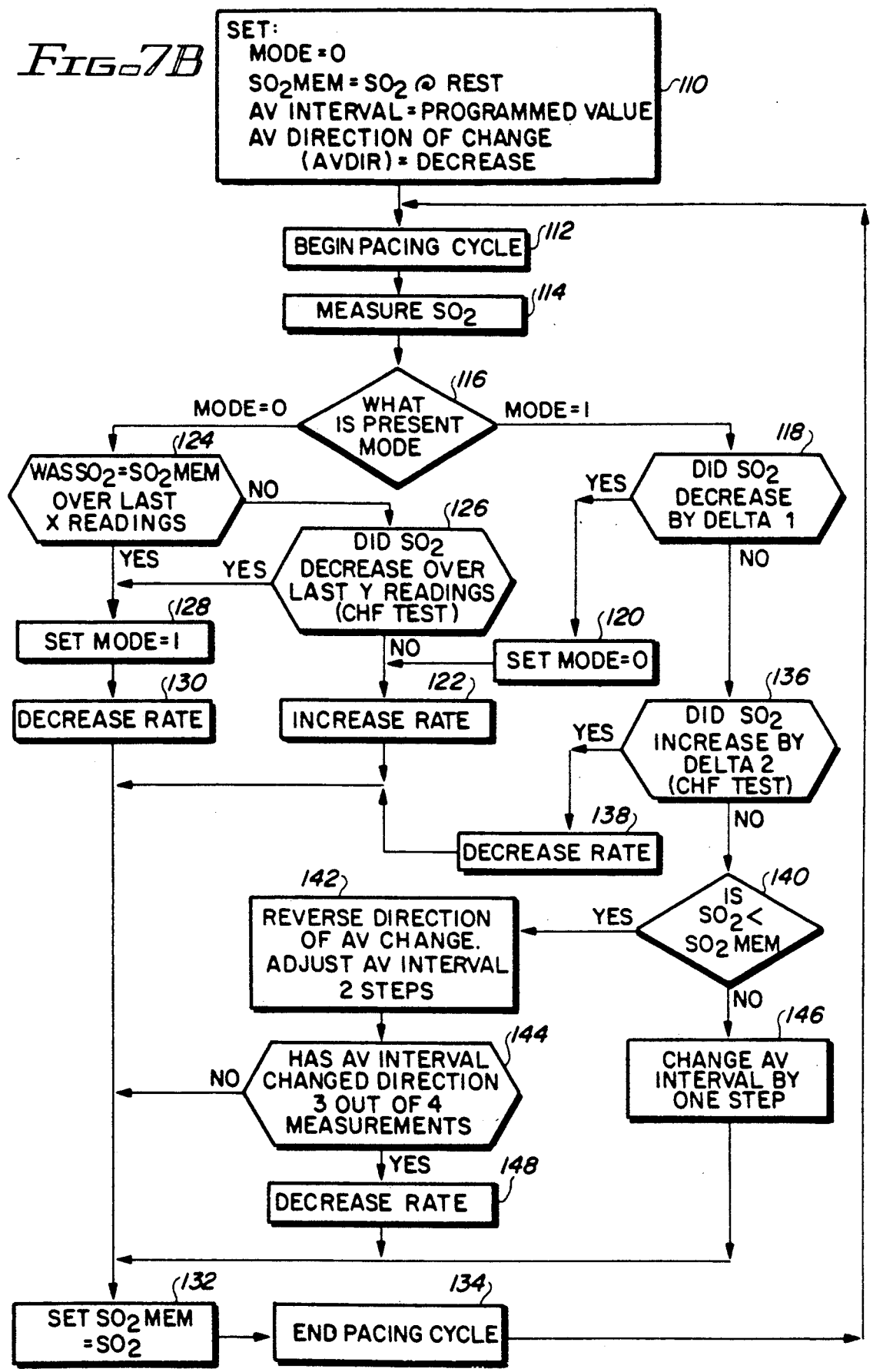

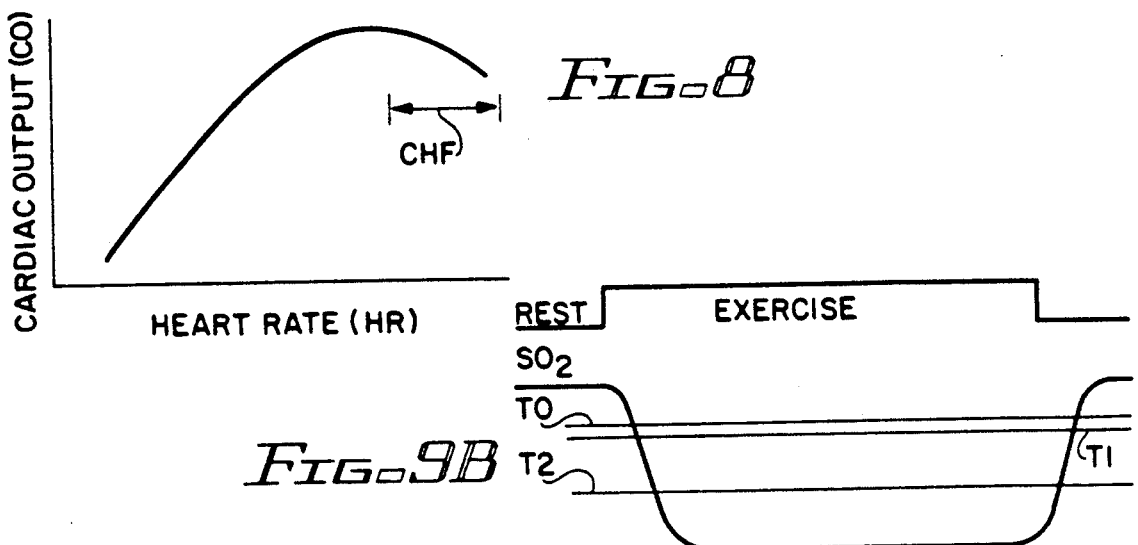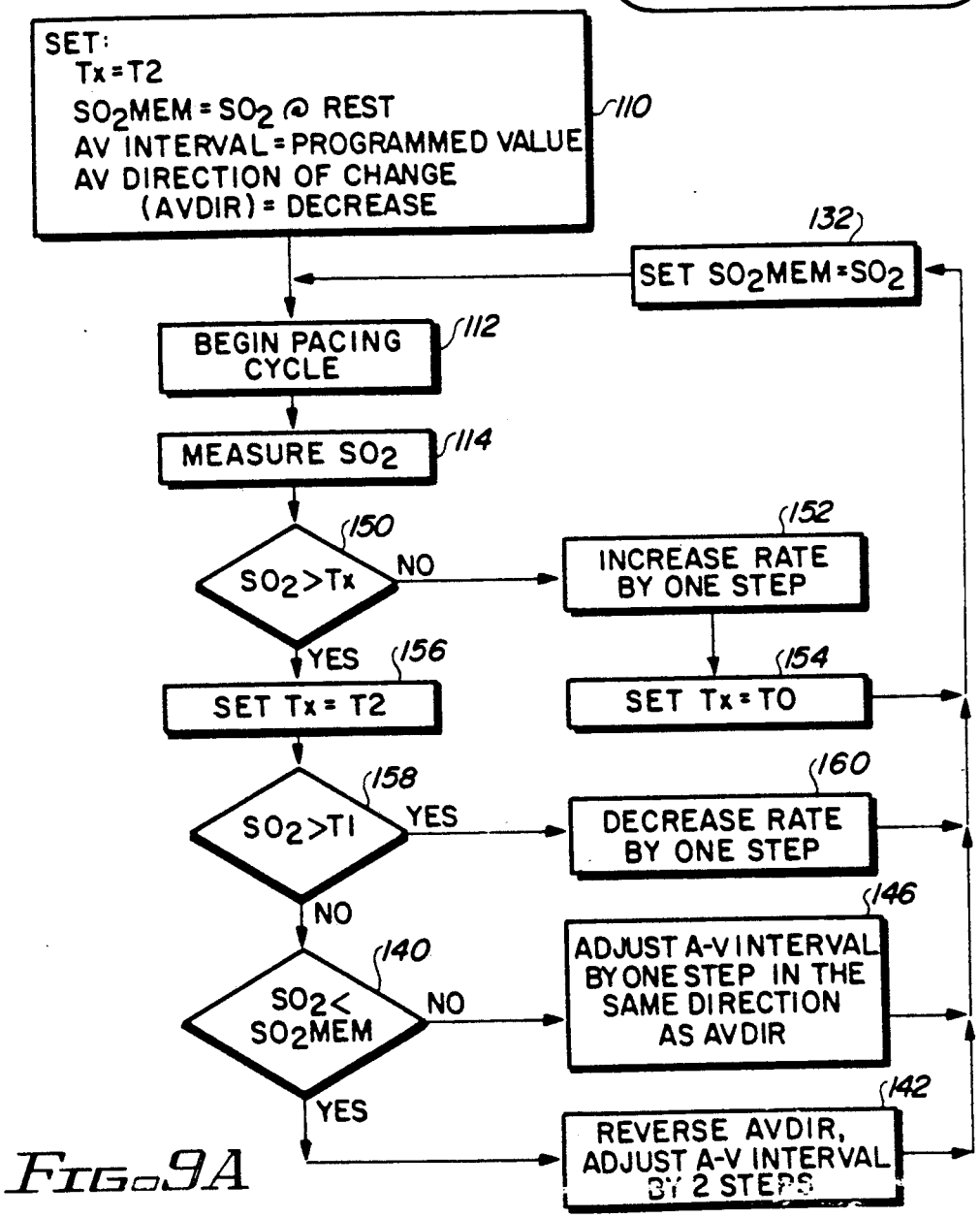

5,024,222

HEMODYNAMICALLY RATE RESPONSIVE PACEMAKER AND METHOD OF AUTOMATICALLY ADJUSTING THE ESCAPE AND A-V INTERVALS

BACKGROUND OF THE INVENTION

The present invention relates generally to implantable medical devices, and more specifically, to rate-responsive cardiac pacemakers which are capable of automatically adjusting their programmable parameters according to physiologic demand.

There has been considerable amount of work done in the area of physiologically controlled rate-responsive pacemakers. Ideally, the physiological pacemaker should vary cardiac rate and, consequently, cardiac output in response to the body's physiological needs. A variety of sensors that indicate the body's state of exercise and/or stress have been proposed for controlling cardiac rate.

Probably the best known physiologic sensor has been the sinus node itself which is responsive to both sympathetic and parasympathetic stimulation (that is, stimulation which both increases and decreases the overall activity of the heart). In a patient with heart block and a functional sinus node, dual-chambered demand pacemakers were able to mimic a normal heart by tracking the sinus node and pacing the ventricles a short atrio-ventricular (A-V) delay later. By preserving A-V synchrony, cardiac output at rest was expected to increase anywhere between 10% and 30%. However, in patients whose sinus node is incompetent (that is, either too slow, non-responsive to exercise stress, or prone to atrial flutter or fibrillation), dual chamber pacemakers could not achieve the higher rates necessary during exercise. In order to maintain cardiac output at all levels of work load, an alternate physiological sensor is required to automatically adjust the stimulation rate independent of atrial activity.

Subsequently, single-chambered, sensor-driven pacemaker systems were developed to sense various physiological parameters as the basis for varying the stimulation rate. These physiological parameters include motion, temperature, Q-T intervals, respiration rate, blood pH, stroke volume, minute ventilation, mixed venous oxygen saturation, the rate of change of ventricular pressure (dP/dt), etc.

These single-chambered rate responsive pacemakers were designed to replace dual chambered devices since it was thought that the 200% to 300% increase in cardiac output associated with an increase in heart rate overshadowed the effects of the 10-30% increase in cardiac output due to maintenance of A-V synchrony. However, the lack of correctly synchronized atrial contractions will mean that the ventricular filling pressure must rise even higher than normal to maintain cardiac output. Thus, pre-existing left and/or right heart failure may be exacerbated by the loss of A-V synchrony. Furthermore, should atrial systole (contraction) occur against a closed A-V valve as a result of retrograde conduction, clinical studies have indicated that, in addition to producing an inappropriately high atrial pressure, a further reduction in cardiac output on the order of 20% may be expected when compared against random atrial contractions.

However, the selection of an appropriate A-V delay at elevated rates is not a simple task. The A-V delay is not constant at all heart rates. Nor is it constant from patient to patient or within different age groups, e.g., an adult heart is very different than a child's heart. Typically, at rest, the A-V delay may vary anywhere between 150 and 250 msec. Once the patient begins to exercise, the A-V delay is estimated to vary anywhere between 125 and 170 msec.

What is needed, therefore, is a hemodynamically responsive pacemaker which can automatically determine both the optimum rate and A-V interval to achieve maximum cardiac output independent of age, patient to patient differences, and heart rate.

SUMMARY OF THE INVENTION

The disadvantages and limitations of the background art discussed above are overcome by the present invention. The present invention comprises a hemodynamically responsive pacemaker which can adjust both the pacing rate and the A-V interval in accordance with a physiological sensor to optimize the cardiac output of the patient's heart. An improvement in cardiac output is determined by detecting an increase in hemodynamic benefit, that is, by detecting an increase in the output of the physiological sensor as a result of a change in a selected parameter, either stimulation rate or A-V delay. If hemodynamic benefit does not increase, then the physiological parameter is said to be maximized and cardiac output is at its optimum. Once the stimulation rate has been adjusted to an optimal rate, the stimulation rate is reduced slightly to detect changes in the physiological parameter as a result of a change in the A-V delay. The pacemaker has the means for alternately adjusting the pacing rate and the A-V interval such that the lowest stimulation rate can be obtained while providing the optimum cardiac output for the patient at a given work load.

The basic pacing system comprises a timing means, which defines a pacing cycle having variable stimulation rate and a variable A-V interval, sense amplifiers for sensing cardiac activity and resetting the timing means accordingly, and stimulation means for generating stimulating pulses in both chambers of the heart. A physiological sensor is used to sense a physiological parameter indicative of the cardiac output of the patient's heart. The system further includes the means for determining an optimal stimulation rate corresponding to a maximum value of the physiological parameter. A first adjusting means triggers the timing means to adjust the stimulation rate in accordance with the physiological parameter to a suboptimal stimulation rate, the suboptimal stimulation rate being at least one discrete step below the optimal stimulation rate. A second adjustment means is used to adjust the A-V interval until the physiological parameter is maximized again while at the sub-optimal rate.

In the preferred embodiment, the present invention comprises the means for determining the optimal hemodynamics by successive approximation. This includes the means for detecting a direction of change of the physiological sensor and, if previous adjustment to the escape or A-V interval was correct, subsequent adjustments will be in the same direction as in the prior cardiac cycle. If the direction of change reverses, then the adjustment means adjusts the escape or A-V interval in the reverse direction than in the prior cardiac cycle. Furthermore, the improvement in cardiac output due to the A-V adjustment allows a further decrease in the stimulation rate by the first adjustment means and a further adjustment of the A-V interval by the second adjustment means, thereby operating the pacemaker at the lowest stimulation rate and conserving the limited battery supply.

In the preferred embodiment, the physiological parameter which is indicative of cardiac output is oxygen saturation of the venous blood. A blood oxygen sensor measures oxygen saturation as a result of the increase in oxygen consumption during exercise. The blood oxygen sensor can be used to increase the stimulation rate, thus providing a increase in oxygen saturation, until oxygen saturation is maximized. The present invention may also be readily employed with other sensors which provide an indication of cardiac output, such as pH of the blood, minute ventilation, and stroke volume.

The present invention further contemplates a method of automatically adjusting both the escape interval (or stimulation rate) and the A-V interval. The method comprises generating stimulating pulses in two chambers of the heart, controlling both the timing for the escape interval and the A-V interval, sensing cardiac activity and resetting the pacing cycle accordingly, and sensing a physiological parameter of the patient's heart. The present invention is capable of determining the optimum stimulation rate corresponding to a "maximum" or "optimum" value of the physiological parameter and adjusting the escape interval until a prescribed limit below the optimum stimulation rate. In the preferred embodiment, this sub-optimal limit is determined by first detecting the rate at which cardiac output is at its optimum and then decreasing the rate by one rate step. After this sub-optimal rate is achieved, the method of the present invention comprises adjusting the A-V interval until the physiological parameter is re-maximized. Finally, the escape interval and the A-V interval may be iteratively re-adjusted, each time re-maximizing the physiological sensor, resulting in the lowest stimulation rate.

Finally, all of the problems and disadvantages of the prior art are overcome in the present invention without incurring any substantial relative disadvantage. By using a physiologic parameter indicative of cardiac output, the present invention is capable of finding the optimum cardiac output regardless of age, individual differences, and heart rate. It will therefore be perceived that the advantages of the present invention result in improving the hemodynamics of the patient while increasing the longevity of the pacemaker by operating at the lowest hemodynamically indicated rate, making the method of the present invention a highly desirable enhancement to implantable cardiac pacemaker therapy.

DESCRIPTION OF THE DRAWINGS

Further features and advantages of the present invention may be more readily understood by reference to the following description taken in conjunction with the accompanying drawings, in which:

FIG. 3 is a timing diagram illustrating the hemodynamics of the normal heart of FIG. 1;

FIG. 6 is a functional block diagram of the preferred embodiment of a hemodynamically rate responsive pacemaker configured in accordance with the teachings of the present invention;

FIGS. 7A and 7B present a flow chart describing the preferred method of automatically adjusting the escape and A-V intervals in a hemodynamically rate responsive pacemaker in accordance with the teachings of the present invention;

FIG. 8 describes an alternate method of automatically adjusting the escape and A-V intervals in a hemodynamically rate responsive pacemaker;

FIG. 9A describes an alternate method of automatically adjusting the rate and the AV interval using an oxygen saturation sensor ($SO_2$) and three thresholds: an optimal threshold (T0), a suboptimal threshold (T1), and a coarse threshold (T2); and FIG. 9B shows the relationship between an oxygen saturation sensor ($SO_2$), workload, and the three thresholds described in the method shown in FIG. 9A.

DETAILED DESCRIPTION OF THE INVENTION

The following description is of the best presently contemplated mode of carrying out the invention. The description is not to be taken in a limiting sense, but is made merely for the purpose of describing the general principles of the invention. The scope of the invention should be determined with reference to the attached claims.

Figure 1:
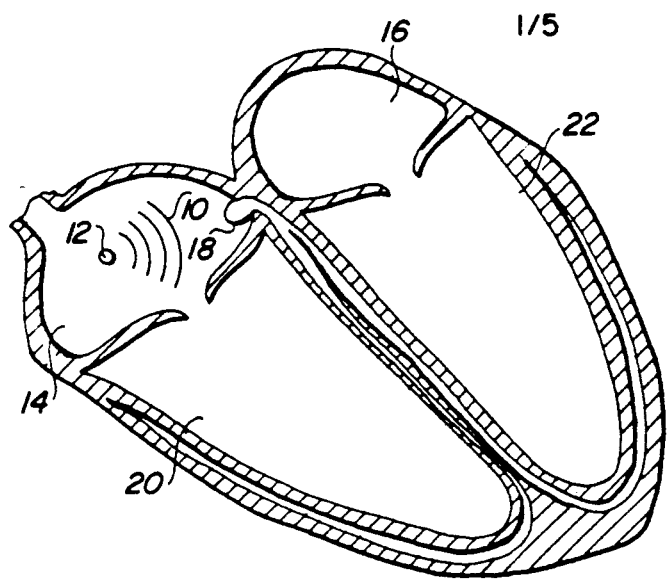
FIG. 1 is a simplified representation of a human heart showing the location of the SA and A-V nodes.

Before describing the present invention in detail, it will be helpful to first have a basic understanding of cardiac anatomy. Each cardiac cycle is initiated by the spontaneous generation of an action potential 10 in the S-A node 12 located in the right atrium 14 as shown in FIG. 1. The action potential 10 then travels rapidly through both the atria 14, 16 and then through the A-V node 18 into the ventricles 20, 22. The propagation of the action potential through the A-V node is delayed by approximately 1/10 of a second to allow the atria to contract ahead of the ventricles thereby pumping blood into the ventricles prior to the very strong ventricular contraction. Thus, the atria act as primer pumps for the ventricles and the ventricles provide the major source of power for moving blood throughout the vascular system.

Figure 2:
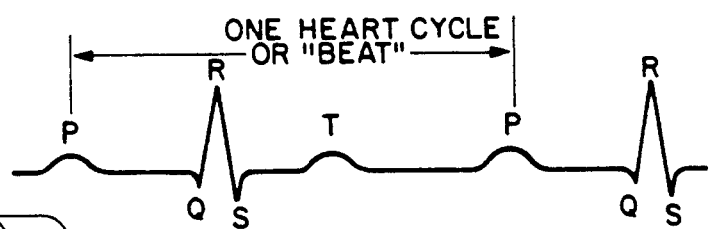
FIG. 2 is a timing diagram illustrating the normal, non-paced operation of the heart of FIG. 1 as sensed through conventional skin ECG electrodes or equivalent.

Shown in FIG. 2 is a representation of various waveforms that are generated as sensed by skin electrodes placed on the chest in response to the above-described activities. A P-wave represents the depolarization of both atria. A Q-R-S-wave commonly referred to as the Q-R-S complex (or simply the R-wave), represents the depolarization of the ventricles. The time between the P-wave and the R-wave corresponds to the delay through the A-V node and the Purkinje system. The T-wave represents the repolarization of the ventricles. This cycle is repeated continuously as the heart pumps the blood throughout the body. Thus, maintaining A-V synchrony (that is, depolarization of the atria followed a short time thereafter by depolarization of the ventricles) is essential if the heart is to efficiently perform its function as a pump in distributing blood throughout the body.

Figure 4:
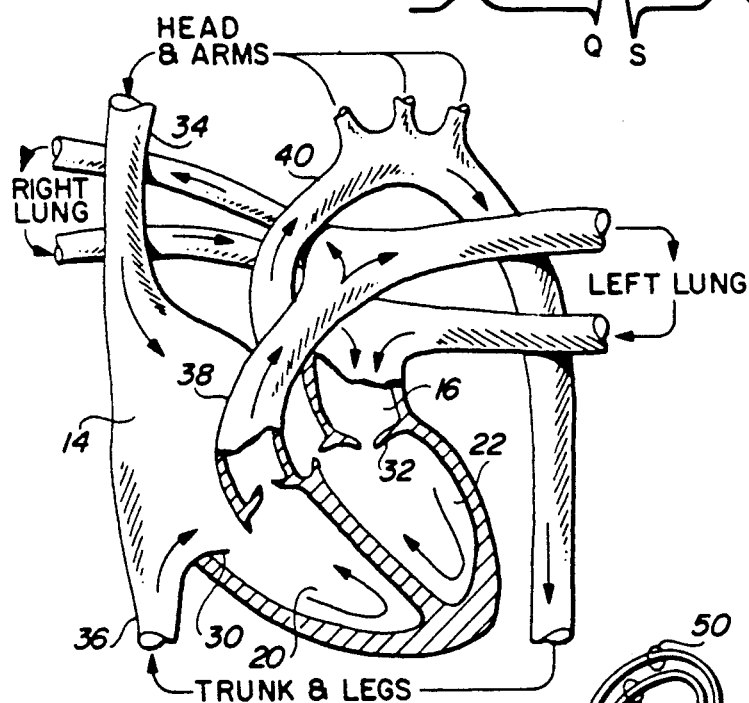
FIG. 4 is a schematic representation of the heart illustrating the main components thereof and the flow of blood therethrough.

Hemodynamically, the cardiac cycle consists of a period of relaxation called diastole, followed by a period of contraction called systole as shown in FIG. 3. During ventricular contraction, the A-V valves 30, 32 as shown in FIG. 4 are closed and large amounts of blood accumulates in the atria 14, 16. As soon as ventricular contraction is over, the higher pressures in the atria immediately push the A-V valves 30, 32 open. Deoxygenated blood enters the right atrium 14 by way of the superior vena cava 34 or the inferior vena cava 36. Approximately 70% of this blood flows directly from the atria into the ventricles even before the atria contract. When the atria finally contract, there is an additional thrust of blood into the ventricles accounting for approximately 30% of the filling of the ventricles during each cardiac cycle. When the right ventricle 20 contracts, the deoxygenated blood is pumped to the lungs via the pulmonary artery 38 where carbon dioxide is removed and replaced with fresh oxygen. Oxygenated blood then returns from the lungs to the left atrium 16. At approximately the same time that the right ventricle 20 contracts, the left ventricle 22 also contracts and pumps the oxygenated blood into the aorta 40 which, in turn, delivers the blood throughout the body.

Therefore, cardiac output is defined as the quantity of oxygenated blood pumped by the left ventricle into the aorta each minute. It is equal to the product of the heart rate and the stroke volume. In the normal heart, both the heart rate and the stroke volume increase to satisfy the body's need for oxygenated blood. It is apparent to one skilled in the art that cardiac output may be increased or "maximized" simply by increasing the stimulation rate, as is done with sensors which detect motion and not stress or workload. However, the "optimum" cardiac output, and thus the "optimum" stimulation rate, can only be determined by optimizing a physiological parameter indicative of cardiac output. In this way, energy is not wasted on stimulation pulses that exceed the optimum stimulation rate.

During exercise, a variety of changes take place in the normal heart: respiration increases, blood flow is diverted to the active skeletal muscles, and cardiac output increases, and therefore, heart rate and/or stroke volume increases. These changes enable an increased amount of oxygen and nutrients to be delivered to the active muscles. In general, the more times the heart beats per minute, the more blood it can pump. But there are limitations to this effect. For example, at elevated rates the period of relaxation between contractions can become so reduced that the blood does not have time to flow adequately from the atria into the ventricles. Furthermore, in patients with poor cardiac function, overstimulation may lead to a fall in cardiac output and, if this is not correctly detected by the sensor, may lead to even higher stimulation rates resulting in a deleterious physiologic failure loop. This might further aggravate an ischemic heart.

The ideal sensor for a hemodynamically responsive pacemaker should be capable of controlling cardiac output linearly with work load and in a "closed-loop" fashion. A closed loop system is one which has a negative feedback mechanism, that is, the system is capable of operating to reduce any divergence of the instantaneous measured value from the optimum value. Presently, only a few of the physiological sensors mentioned are capable of either proportional control or closed-loop control.

For example, Plicchi et. al, in U.S. Pat. No. 4,596,251, teaches the use of minute ventilation (that is, the impedance between two electrodes to detect tidal volume and respiration rate) to proportionately control the pacing rate; as minute ventilation increases (indicating an increase in oxygen demand), rate is also increased, and vice versa. Minute ventilation has been shown to be a better sensor than respiration rate alone because it is proportional to oxygen consumption up to the anaerobic threshold. For example, in the absence of physical activity (such as sleep), minute ventilation and oxygen uptake are reduced due to the minimal metabolic demand of the body even though the respiration rate may increase. In order to increase minute ventilation in response to an increase in oxygen demand, athletes are trained to increase tidal volume more than the respiratory rate. U.S. Pat. No. 4,596,251 is hereby incorporated herein by reference.

Olson, in U.S. Pat. No. 4,535,774, teaches a rate-responsive pacemaker which alters the pacing rate linearly according to stroke volume. In the absence of an increase in sinus rate, exercise induced stroke volume will increase (up to 50%) due to circulating catecholamines (which enhance contractility of the heart) and the increase in venous return from the muscles. This increase in stroke volume also has a linear relationship with work load. U.S. Pat. No. 4,535,774, is hereby incorporated herein by reference.

Wirtzfeld, et al in U.S. Pat. No. 4,399,820 teaches that oxygen saturation of the blood has an inverse relationship to cardiac rate (as $SO_2$ decreases during exercise, the frequency of stimulation should be increased, and vice versa), thus indicating a negative feedback system which is ideal for a closed-loop system. U.S. Pat. No. 4,399,820 is hereby incorporated herein by reference.

Figure 5:
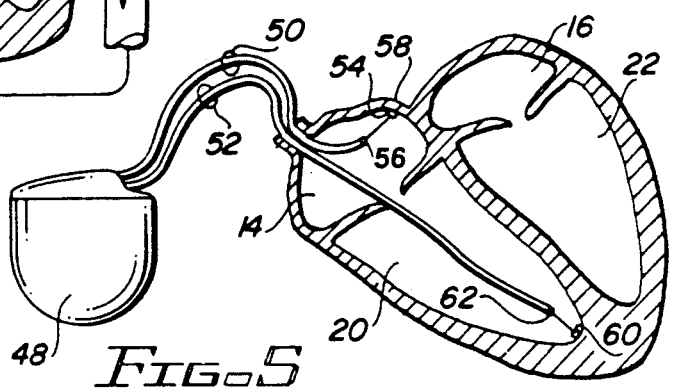
FIG. 5 is a simplified representation of the heart showing the manner in which a pacemaker is connected thereto through insertion of bipolar leads into both the right atrium and the right ventricle.

FIG. 5 shows a simplified diagram of one way an implanted pacemaker 48 may make electrical contact with the heart. Two (2) bipolar leads 50, 52 are being directed into a separate chamber of the right heart. A bipolar lead comprises a single filar that includes two (2) electrically insulated conductors. A first conductor of bipolar lead 50 is electrically connected to a distal tip 54. A second conductor is electrically connected to a conductive ring electrode 56 approximately one inch from the distal tip 54. The distal tip 54 is typically placed in a cavity of the right atrium 14 referred to as the atrial appendage 58. Similarly, a bipolar lead 52 having a distal tip 60 and a conductive ring electrode 62 are placed in the apex of the right ventricle 20. Alternately, the leads may be unipolar leads or other multi-pole leads, all of which are known in the art.

A block diagram of the present invention which combines dual chamber pacing with a rate responsive pacemaker 48 is shown in FIG. 6. Briefly, the rate responsive pacemaker functions as follows. The pacemaker 48 includes a conventional pacemaker chip 70 which has a pulse generator 72 for generating stimulation pulses 74, 74' to the heart. Sense amplifiers 76 are employed to sense cardiac events and to communicate this information to timing and control circuitry 78. The timing and control circuity 78 control the timing and sequence of the stimulation pulses 74, 74' in addition to the inhibition of a stimulus in the event of sensed cardiac signal. Telemetry circuits 80 are employed to receive programming signals from an external programmer 82 which are then stored in a memory device 84. The memory device 84, in turn, is coupled to the timing and control circuitry 78 as well as a rate response (RR) processor 86 and a sensor on/off switch 88.

The external programmer 82 is used to non-invasively send programming signals the telemetry circuits 80. These programming signals are depicted symbolically as the wavy line 90 in FIG. 6. It is noted that such signals may be sent bi-directionally between the external programmer 82 and the pacemaker 48. In this way, the external programmer 82 can non-invasively alter the pacemaker's programmable parameters.

A more complete description of the pacemaker chip 70, the external programmer 82, and their operation may be found in several patents. For example, note U.S. Pat. Nos. 4,572,193 to Mann, et al. entitled "DDI Programmable Cardiac Tissue Stimulator" and 4,809,697 to Causey, et al. entitled "Interactive Programming and Diagnostic System For Use With An Implantable Pacemaker." While not disclosing the exact same pacemaker chip or circuits which are used in the preferred embodiment of the present invention, these patents nonetheless disclose the primary components of a conventional pacing system and teach the basic operation thereof. U.S. Pat. Nos. 4,572,193 and 4,809,697 are hereby incorporated herein by reference.

The pacing system further includes a rate responsive sensor 92 for sensing the physiological needs of the patient. In the preferred embodiment, the rate responsive sensor 92 is an oxygen saturation ($SO_2$) sensor. The oxygen saturation sensor may be placed in the ventricle, as shown in FIG. 6, or in the atrium. However, the present invention is not restricted to this type of sensor but merely to a sensor that is capable of reliably detecting a physiological parameter indicative of cardiac output and, thus, the hemodynamic needs of the patient. Hereinafter, the sensor which is used to change the pacing rate shall simply be referred to as the "RR sensor". Furthermore, although the RR sensor 92 is shown in FIG. 6 as being included within the pacemaker lead, it is understood that the RR sensor 92 could also be included within the pacemaker 48 itself or otherwise placed external to the pacemaker 48.

In the preferred embodiment, the output of the RR sensor 92 is measured during each pacing cycle by the sensor signal processing circuitry 94 which is capable of converting the raw signal to a digital signal. The RR processor 86 in turn converts the digital signal to a sensor-indicated rate signal 96. This conversion may be accomplished in several ways using conventional techniques: typically, by a transfer curve, a look up table stored or programmed into the memory, algorithmically, or in hardware or software, or a combination thereof. In the preferred embodiment, the rate response sensor 92 acts in a closed loop fashion. As oxygen saturation decreases during exercise, the frequency of stimulation is increased.

As the oxygen saturation sensor increases with an increase in stimulation rate, the previous value is compared to the current value to detect any hemodynamic benefit. Once the oxygen saturation sensor no longer detects any hemodynamic benefit, the sensor has reached its maximum value and the stimulation rate, which stops increasing, is said to have reached its optimum rate. The RR processor 86 also has the capability of producing a sensor-indicated A-V time interval 98 as follows: once the stimulation rate has reached its optimum rate, the stimulation rate is decreased slightly to enable detection of hemodynamic improvement during the AV adjustment. The A-V delay is adjusted in the direction that also tends to maximize the physiological sensor until an "optimum" A-V interval is found at that particular rate. Following the optimum AV interval, the stimulation rate may be further decreased, and the AV interval adjusted further. After each adjustment of the A-V interval, the rate is decreased by one step until a coarse threshold is reached indicating that the rate has dropped too low for that exercise level. It should be noted that the coarse threshold also permits the system to jump out of the A-V loop due to a sudden change in the physiological sensor to permit re-adjustment of the stimulation rate. When exercise ends, the stimulation rate will naturally decrease until either the rest rate or a new exercise level is achieved. Therefore, it may be seen that the present invention does not simply increase cardiac output by merely increasing the rate, but rather it "optimizes" cardiac output by detecting the maximum physiological sensor output and thereby eliminates any wasted energy due to unnecessary stimulation.

Functionally, the pulse generator 72 generates stimulation pulses at a rate determined by a rate control signal 99 and at an A-V delay is determined by an A-V delay control signal 100. These pulses, in turn, are delivered to the heart through the leads and in a conventional manner. The electrical signals occurring within the heart, such as P-waves and R-waves, are sensed by the sense amplifiers 76 via the leads and presented to the timing and control circuitry 78. Hence, for example, when programmed in a demand mode of operation, the pacemaker chip 70 is able to inhibit the generation of a stimulating pulse 74 or 74' when natural cardiac activity is sensed within a designated time period, in conventional manner.

In operation, the rate responsive pacer may operate in either a SENSOR ON mode or a SENSOR OFF mode which can be selected by an appropriate programming signal 90 received from the external programmer 82. Switch 88 is a double pole, single throw switch and is employed to select the appropriate rate control signal 99 and A-V delay control signal 100: either the programmed base rate signal 101 and the programmed A-V delay signal 102 (during SENSOR OFF mode) or the sensor-indicated rate signal 96 and the sensor-indicated A-V delay signal 98 as determined by the RR processor 86 (during the SENSOR ON mode).

Figure 7A:
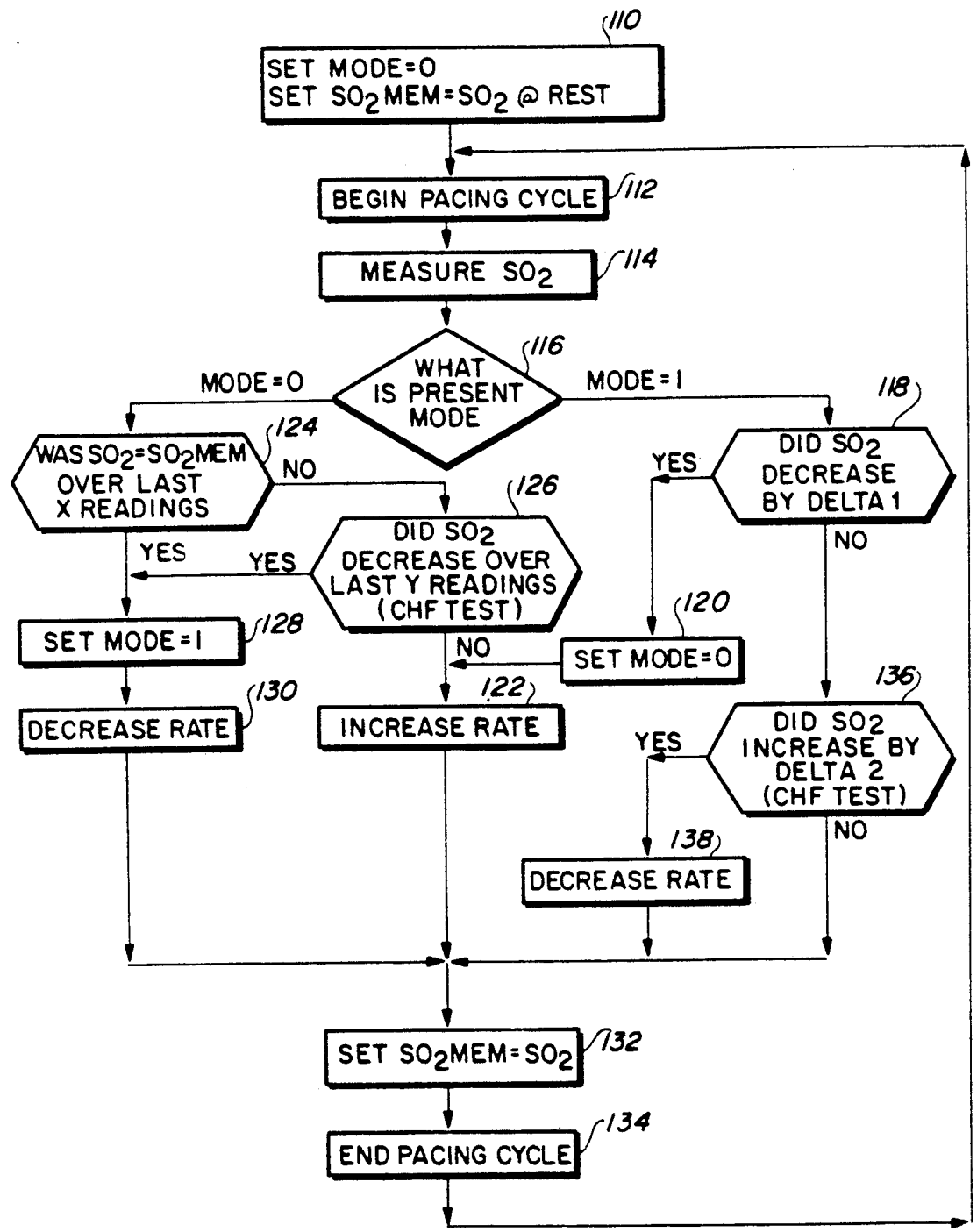

FIG. 7A describes the basic principles of a method of adjusting the rate using an SO2 sensor. At 110 variables are initialized: mode can be set to either "0" or "1" and the value of the $SO_2$ sensor at rest is stored into memory, $SO_2MEM$. At 112, a stimulus is delivered to the ventricles and the pacing cycle begins. After the stimulus, the $SO_2$ level is measured at 114 and the present mode is checked at 116. If the mode has been previously set to a "1", then the change in value of the $SO_2$ sensor is compared to a first prescribed delta at 118. This delta is used to detect a sudden decrease in $SO_2$ as a result of an increase in exercise. If the change in $SO_2$ has decreased beyond the first prescribed delta, then the mode is set to "0" at 120 and rate is increased at 122.

If on the other hand, the present mode was already set to "0", the value of the $SO_2$ sensor would be compared at 124 to the last "x" values of the $SO_2$ sensor which were stored in memory, $SO_2MEM$. This decision block is used to detect whether the current value of the $SO_2$ sensor has reached a maximum, i.e., if the value of the $SO_2$ sensor has not shown an increase over the last "x" readings, then a maximum has been reached and the rate will be decreased at 130. Thus, the system tends to operate at the lowest stimulation rate.

If the $SO_2$ level has decreased below $SO_2MEM$ at 124 as a result of exercise, a test is performed at 126 to detect whether the patient is in congestive heart failure (CHF), which will be explained below. If the patient is not in CHF, the rate will be increased at 122. Finally, the current value of the $SO_2$ sensor is stored in $SO_2MEM$ at 132 for future reference and the pacing cycle ends at 134. Therefore, it may readily be seen from the above description that regardless of what the mode is initially set to, a sudden increase in exercise will result in an increase in rate.

Patients who are in congestive heart failure (CHF) also have a positive response to increases in rate during exercise, however, after a critical point on their particular cardiac output curve as shown in FIG. 8, a negative hemodynamic effect occurs with a further increase in rate. Therefore, CHF patients are tested at 126 to determine whether their $SO_2$ level has decreased over the last "y" readings. If so, the mode is set to "1" at 128 and the rate is decreased at 130 which results in an increase in $SO_2$. On the next pacing cycle, the mode is checked again at 116 and the change in value of the $SO_2$ sensor is compared to the first prescribed delta at 118. Since the $SO_2$ level has increased, the change in value of the $SO_2$ sensor is compared to a second prescribed delta at 136. If the $SO_2$ level has increased by the second prescribed delta, indicating that the patient was in CHF, then the rate will be decreased further at 138. The current value of the $SO_2$ sensor is again stored in $SO_2MEM$ at 132 and the pacing cycle ends at 134.

FIG. 7B describes the preferred method of automatically adjusting the rate and the AV interval using an $SO_2$ sensor of the present invention. First, the rate is adjusted to its optimum level as described above. When the maximum $SO_2$ level is found at 124, then the mode is changed to "1" at 128 and the rate is decreased at 130. This decreasing of rate provides an $SO_2$ level which is slightly below maximum to enable detection of an increase in $SO_2$ due to AV adjustment.

On the next pacing cycle, the $SO_2$ level is checked at 118 for a sudden change in $SO_2$ due to a higher work load. If none is detected, the patient is tested for CHF at 136. If CHF is not present, then the AV interval may be adjusted. At 140, the $SO_2$ level is compared to $SO_2MEM$ to determine if $SO_2$ has decreased. Since a decrease in $SO_2$ occurred as a result of the rate decrease, the processor reverses direction of AV interval and adjusts the AV interval by two steps at 142. At 144 the number of changes in direction are tested to determine if a maximum has been found, i.e., if the change of direction toggles back in forth several times in a short period, then a maximum has been found. If it turns out that this is the wrong direction of AV change, then on the next pacing cycle the direction of change will reverse again. When the direction of change is correct, the AV interval is adjusted in the same direction each pacing cycle at 146. When the AV interval is adjusted too far in one direction, the level of $SO_2$ will drop, causing a reversal of the direction of change of AV adjustments at 142. After at least three reversals in 4 measurements, a maximum is detected at 144 and the rate is decreased at 148. On the next pacing cycle, the mode remains in "1", and a further adjustment in AV interval is performed at the lower stimulation rate. This process will continue until the $SO_2$ drops below the first prescribed delta at 118 such that the mode switches back to mode "0" and enable a rate increase.

FIGS. 9A and 9B describe an alternative method of automatically adjusting the rate and the AV interval using an $SO_2$ sensor of the present invention. FIG. 9B shows three thresholds, T0, T1 and T2, relative to an $SO_2$ level during an exercise interval. Threshold T0 corresponds to an appropriate or an optimal stimulation rate for that particular work load. Threshold T1 corresponds to a suboptimal rate for that particular work load. The suboptimal rate is used to provide sufficient dynamic range while adjusting the A-V delay. And threshold T2 provides a coarse threshold, below which a rate increase is initiated.

In FIG. 9A, variables are initialized at 110: the threshold variable, Tx, is set to T2 (the coarse threshold indicative of a need for a rate increase), the A-V interval is set to the programmed value, the direction of change of the A-V interval is set (arbitrarily) to decrease, and the value of the $SO_2$ sensor at rest is stored into memory, $SO_2MEM$.

At 112, a stimulus is delivered to the ventricles and the pacing cycle begins. After the stimulus, the $SO_2$ level is measured at 114. The level of the $SO_2$ is compared to Tx, i.e., the coarse threshold at 150. If the $SO_2$ level is less than Tx, then the rate is increased at 152 and the threshold, Tx, is set to T0 at 154, T0 being a predetermined optimum value. Once the $SO_2$ level is greater than T0, then the threshold, Tx, is set back to the coarse value, T2, at 156. The $SO_2$ level is then compared to a third threshold, T1, at 158 (T1 being the suboptimal threshold). If the level of $SO_2$ is greater than this suboptimal threshold, T1, then the rate is decreased at 160. Once the level of $SO_2$ is below the suboptimal threshold, T1, then the A-V interval may be adjusted similar to the approach in FIG. 7B. As soon as the level of $SO_2$ drops below the coarse threshold, T2, A-v adjustment will stop and rate adjustment will repeat.

In summary, the stimulation rate is adjusted first until it is at its optimum value. The stimulation rate is reduced to a level slightly below the optimum value, at which point the A-V delay is adjusted until the physiological sensor has reached a maximum. This cycle can repeat indefinitely in a successive approximation manner. In this way, the pacemaker can hone in on the optimum hemodynamics at the lowest stimulation rate, thus, saving energy and preserving battery life.

It will therefore be perceived that the advantages of the present invention result in a hemodynamically responsive system which can automatically determine both the optimum rate and the A-V interval to achieve the optimum cardiac output independent of age, patient-to-patient differences, and heart rate. It can further be seen that the lowest stimulation rate can be obtained while providing the optimum cardiac output. Thus, the longevity of the pacemaker is extended while a higher quality of life is provided for the patient, making the method of the present invention a highly desirable enhancement to implantable cardiac therapy.

Although an exemplary embodiment of the present invention has been shown and described, it will be apparent to those having ordinary skill in the art that a number of changes, modifications, or alterations to the invention as described herein may be made none of which depart from the spirit of the present invention. All such changes, modifications, and alterations should therefore be seen as within the scope of the present invention.

What is claimed is:

1. In a dual chamber pacemaker, a system for optimizing cardiac output of a patient's heart, the pacemaker having a pulse generator for generating atrial and ventricular stimulation pulses and timing means for defining a pacing cycle having a stimulation rate and a A-V time interval between the atrial and the ventricular stimulation pulses, the stimulation rate and the A-V interval being adjustable in discrete steps, the system comprising:

a physiological sensor for sensing, during at least one cardiac cycle, a physiological parameter indicative of the cardiac output of the patient's heart;

means for determining an optimal stimulation rate corresponding to a maximum value of the physiological parameter;

means for adjusting the stimulation rate to a suboptimal stimulation rate, the suboptimal stimulation rate being at least one discrete step below the optimal stimulation rate;

means for determining an optimal A-V time interval, the optimal A-V time interval corresponding to a maximum value of the physiological parameter while the stimulation rate equals the suboptimal stimulation rate; and means for adjusting the A-V time interval to the optimal A-V time interval while the stimulation rate is at the suboptimal stimulation rate.

2. The system of claim 1, further comprising:

means for decreasing the stimulation rate by at least one discrete step subsequent to achieving the optimal A-V interval; and means for determining a current optimal A-V time interval, the current optimal A-V time interval corresponding to the maximum value of the physiological parameter;

wherein the means for adjusting the A-V time interval includes means for adjusting the A-V time interval to the current optimal A-V time interval.

3. The system of claim 2, further comprises:

means for detecting a decrease in the physiological parameter below a predetermined threshold;

means for controlling the decreasing means and the means for adjusting the A-V time interval until the physiological parameter decreases below the predetermined threshold, whereby cardiac output is optimized at a decreased stimulation rate.

4. In a dual chamber pacemaker, a system for optimizing cardiac output of a patient's heart, the pacemaker having a pulse generator for generating atrial and ventricular stimulation pulses and timing means for defining a pacing cycle having a stimulation rate and a A-V time interval between the atrial and the ventricular stimulation pulses, the stimulation rate and the A-V interval being adjustable in discrete steps, the system comprising:

a physiological sensor for sensing, during at least one cardiac cycle, a physiological parameter indicative of the cardiac output of the patient's heart;

means for adjusting the stimulation rate to an optimal stimulation rate, the optimal stimulation rate corresponding to a maximum value of the physiological parameter;

means for decreasing the stimulation rate from the optimal stimulation rate by at least one discrete step to obtain a suboptimal stimulation rate; and means for adjusting the A-V time interval to an optimal A-V time interval while the stimulation rate is at the suboptimal stimulation rate, the optimal A-V time interval corresponding to a maximum value of the physiological parameter while stimulating at the suboptimal stimulation rate.

5. The system of claim 4, wherein the means for adjusting the stimulation rate comprises:

means for detecting a decrease in the physiological parameter below a predetermined threshold;

means for determining an optimal value of the physiological parameter, the optimal value of the physiological parameter being a maximum value of the physiological parameter obtained when the physiological parameter is constant for a predefined number of consecutive pacing cycles; and means for increasing the stimulation rate, in response to the detecting means detecting a decrease in the physiological parameter below the predetermined threshold, the stimulation rate being increased at least one step per cardiac cycle until the maximum value of the physiological parameter is reached.

6. The system of claim 4, wherein the means for adjusting the A-V time interval comprises means for determining an A-V direction of change.

7. The system of claim 6, wherein the means for determining an A-V direction of change comprises:

memory means for storing an A-V direction of change;

means for determining a sensor direction of change between two successive values of the physiological sensor; and means for reversing the A-V direction of change when the sensor direction of change is negative.

8. The system of claim 7, wherein the means for adjusting the A-V time interval further comprises:

means for determining an optimal value of the physiological parameter, the optimal value of the physiological parameter being the maximum value of the physiological parameter obtained when the A-V direction of change reverses at least three times during a predefined number of consecutive pacing cycles; and means for increasing the A-V time interval in the A-V direction of change by at least "n" discrete steps per cardiac cycle, where "n" is an integer, until the maximum value of the physiological parameter is reached.

9. The system of claim 8, wherein "n" steps equals one step when the sensor direction of change is positive and two steps when the sensor direction of change is negative.

10. The system of claim 4, wherein the physiological parameter is mixed venous oxygen saturation of the blood.

11. The system of claim 4, wherein the physiological parameter is minute ventilation.

12. The system of claim 4, wherein the physiological parameter is stroke volume.

13. In a rate responsive pacemaker, a system for adjusting the stimulation rate of the heart of a patient with congestive heart failure, the pacemaker having a pulse generator for generating stimulation pulses to the patient's heart, and timing means for generating a variable stimulation rate, the system comprising:

a physiological sensor for sensing a physiological parameter having a value indicative of the physiological needs of the patient's heart, wherein a decrease in the value of the physiological parameter indicates a need for an increase in heart rate;

means for adjusting the stimulation rate in response to a sensed change in the physiological parameter;

a first detection means for detecting a decrease in the value of the physiological parameter as a result of an increase in the stimulation rate, whereby congestive heart failure is detected; and means for decreasing the stimulation rate in response to the first detection means.

14. The system of claim 13, further comprising:

a second detection means for detecting an increase in the value of the physiological parameter as a result of a decrease in the stimulation rate; and means for decreasing the stimulation rate in response to the second detection means.

15. The system of claim 14, wherein the adjusting means comprises:

a third detection means for detecting a decrease in the value of the physiological parameter below a predetermined threshold;

a fourth detection means for detecting an increase in the value of the physiological parameter as a result of an increase in the stimulation rate; and means for increasing the stimulation rate in response to the third and fourth detection means.

16. The system of claim 15, wherein the physiological parameter is mixed venous oxygen saturation of the blood.

17. In a dual chamber pacemaker, a method for optimizing cardiac output of a patient's heart, the pacemaker having a pulse generator for generating atrial and ventricular stimulation pulses and timing means for defining a pacing cycle having a stimulation rate and a A-V time interval between the atrial and the ventricular stimulation pulses, the stimulation rate and the A-V interval being adjustable in discrete steps, the method comprising the steps of:

a) sensing, during at least one cardiac cycle, a physiological parameter indicative of the cardiac output of the patient's heart;

b) determining an optimal stimulation rate corresponding to a maximum value of the physiological parameter;

c) adjusting the stimulation rate to a suboptimal stimulation rate, the suboptimal stimulation rate being at least one discrete step below the optimal stimulation rate;

d) determining an optimal A-V time interval, the optimal A-V time interval corresponding to a maximum value of the physiological parameter while the stimulation rate equals the suboptimal stimulation rate; and e) adjusting the A-V time interval to the optimal A-V time interval while the stimulation rate is at the suboptimal stimulation rate.

18. The method of claim 17, further comprising the steps of:

f) decreasing the stimulation rate by at least one discrete step subsequent to achieving the optimal A-V interval;

g) determining a current optimal A-V time interval, the current optimal A-V time interval corresponding to the maximum value of the physiological parameter while stimulating the heart at the stimulation rate determined in step (f); and h) adjusting the A-V time interval to the current optimal A-V time interval while the stimulation rate is at the rate determined in step (f).

19. The method of claim 17, further comprising the steps of:

detecting a decrease in the physiological parameter below a predetermined threshold;

repeating steps (f), (g) and (h) until the physiological parameter decreases below the predetermined threshold, whereby cardiac output is optimized at a decreased stimulation rate.

20. The method of claim 19, wherein the step of adjusting the stimulation rate comprises:

detecting a decrease in the physiological parameter;

increasing the stimulation rate in response to the detecting means; and determining a maximum value of the physiological parameter, the maximum value of the physiological parameter obtained when the physiological parameter is constant for a predefined number of consecutive pacing cycles.

21. The method of claim 20, wherein the step of determining an A-V direction of change comprises the steps of:

storing an A-V direction of change;

determining a sensor direction of change between two successive values of the physiological sensor; and reversing the A-V direction of change when the sensor direction of change is negative.

22. The method of claim 19, wherein the means for adjusting the A-V time interval comprises the step of determining an A-V direction of change.

23. The method of claim 22, wherein the means for adjusting the A-V time interval further comprises:

determining a maximum value of the physiological parameter, the maximum value of the physiological parameter obtained when the A-V direction of change reverses at least three times during a predefined number of consecutive pacing cycles; and increasing the A-V time interval in the A-V direction of change by at least one step when the sensor direction of change is positive and by at least two steps when the sensor direction of change is negative.

24. In a dual chamber pacemaker, a method for optimizing cardiac output of a patient's heart, the pacemaker having a pulse generator for generating atrial and ventricular stimulation pulses and timing means for defining a pacing cycle having a stimulation rate and a A-V time interval between the atrial and the ventricular stimulation pulses, the stimulation rate and the A-V interval being adjustable in discrete steps, the method comprising the steps of:

sensing, during at least one cardiac cycle, a physiological parameter indicative of the cardiac output of the patient's heart;

adjusting the stimulation rate to an optimal stimulation rate, the optimal stimulation rate corresponding to a maximum value of the physiological parameter;

decreasing the stimulation rate from the optimal stimulation rate by at least one discrete step to obtain a suboptimal stimulation rate; and adjusting the A-V time interval to an optimal A-V time interval while the stimulation rate is at the suboptimal stimulation rate, the optimal A-V time interval corresponding to a maximum value of the physiological parameter.

25. In a rate responsive pacemaker, a method for adjusting the stimulation rate of the heart of a patient with congestive heart failure, the pacemaker having a pulse generator for generating stimulation pulses to the patient's heart, and timing means for generating a variable stimulation rate, the method comprising the steps of:

sensing a value of a physiological parameter indicative of the physiological needs of the patient's heart, wherein a decrease in the value of the physiological parameter indicates a need for an increase in heart rate;

adjusting the stimulation rate in response to a sensed change in the physiological parameter;

detecting a decrease in the value of the physiological parameter as a result of an increase in the stimulation rate, whereby congestive heart failure is detected; and decreasing the stimulation rate in response to the detected decrease in the value of the physiological parameter as a result of the increase in the stimulation rate.

26. The method of claim 25, further comprising the steps of:

detecting a increase in the value of the physiological parameter as a result of a decrease in the stimulation rate; and decreasing the stimulation rate in response to the detected increase in the value of the physiological parameter as a result of the decrease in the stimulation rate.

* * * * *